US00PP35496P2

(12) United States Plant Patent
Lucas et al.

(10) Patent No.: US PP35,496 P2
(45) Date of Patent: Nov. 21, 2023

(54) ***HAKONECHLOA* PLANT NAMED 'LUCMULL'**

(50) Latin Name: *Hakonechloa macra*
Varietal Denomination: LUCMULL

(71) Applicant: Knoll Gardens Ltd., Wimborne (GB)

(72) Inventors: Neil Lucas, Wimborne (GB); Ross Humphrey, Wimborne (GB)

(73) Assignee: KNOLL GARDENS LTD., Dorset (GB)

( * ) Notice: Subject to any disclaimer, the term of this patent is extended or adjusted under 35 U.S.C. 154(b) by 0 days.

(21) Appl. No.: 18/124,558

(22) Filed: Mar. 21, 2023

Related U.S. Application Data

(60) Provisional application No. 63/328,059, filed on Apr. 6, 2022.

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
(74) *Attorney, Agent, or Firm* — Penny J. Aguirre

(57) ABSTRACT

A new and unique cultivar of *Hakonechloa* plant named 'LUCMULL' that is characterized by its yellow and green variegated foliage colors that develop very vibrant red tints from the tips of the leaves downwards in summer into fall and its slow growth habit.

2 Drawing Sheets

Botanical classification: *Hakonechloa macra.*
Varietal designation: 'LUCMULL'.

CROSS REFERENCE TO A RELATED APPLICATION

This application claims priority to a U.S. Provisional Patent Application, Application No. 63/328,059, filed Apr. 6, 2022 under 35 U.S.C. 119(e), the entire contents of which is incorporated by reference herein. This application is related to a European plant breeders' rights application filed on Oct. 14, 2021, application No. 2021/2575. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Hakonechloa macra* and will be referred to hereafter by its cultivar name, 'LUCMULL'. 'LUCMULL' represents a new ornamental grass grown for landscape use.

The Inventors discovered the new cultivar in May of 2005 as a naturally occurring shoot mutation of *Hakonechloa macra* 'Aureola' (not patented) that was growing outdoors in a garden in Wimborne, Dorset, United Kingdom.

Asexual propagation of the new cultivar was first accomplished under the direction of the inventor by division in June of 2005 in Wimborne, Dorset, United Kingdom. Asexual propagation by division and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'LUCMULL' as a unique cultivar of *Hakonechloa.*

1. 'LUCMULL' exhibits yellow and green variegated foliage colors that develope very vibrant red tints from the tips of the leaves downwards in summer into fall.
2. 'LUCMULL' exhibits a slow growing plant habit.

The female parent of 'LUCMULL' differs from 'LUCMULL' in having leaves that are yellow and green in color all year with no red coloration. 'LUCMULL' can also be compared to cultivar *Hakonechloa* 'Naomi' (U.S. Plant Pat. No. 19,897). 'Naomi' is similar to 'LUCMULL' in foliage colors. 'Naomi' differs from 'LUCMULL' in having dull, less vibrant red foliage colors in fall.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosure of first sale date on the CPVO plant breeder's application refers to distribution of trial plants only. Disclosures include website listings by Genesis-Plant Marketing and Back Mountain Bloomers on Facebook.

BRIEF DESCRIPTION OF THE DRAWINGS

The accompanying color photographs illustrate the overall appearance and distinct characteristics of the new cultivar of *Hakonechloa* as grown outdoors at a nursery in Wimborne, Dorset, United Kingdom. The photos were taken of a 3-year-old plant of 'LUCMULL' as grown outdoors in a 30-cm container.

The photograph in FIG. 1 provides a view of the foliage in fall.

Figure 1:
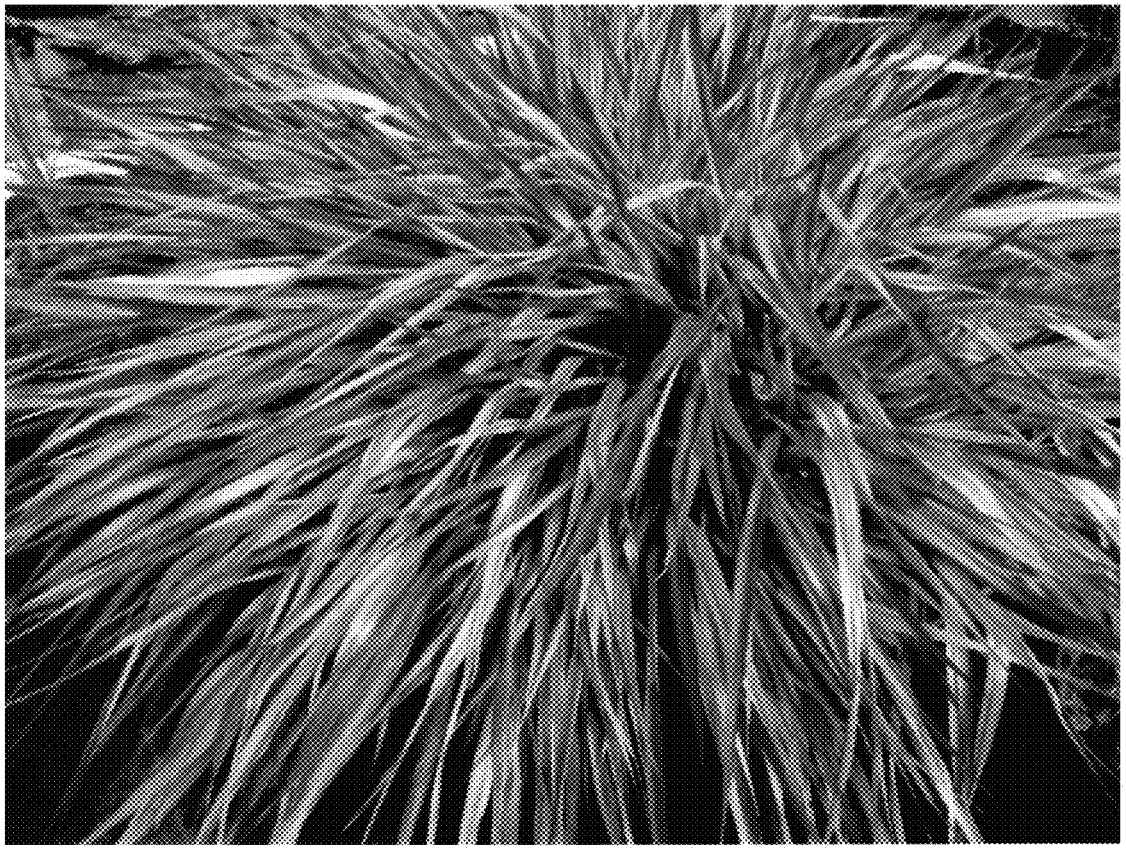
Figure 2:
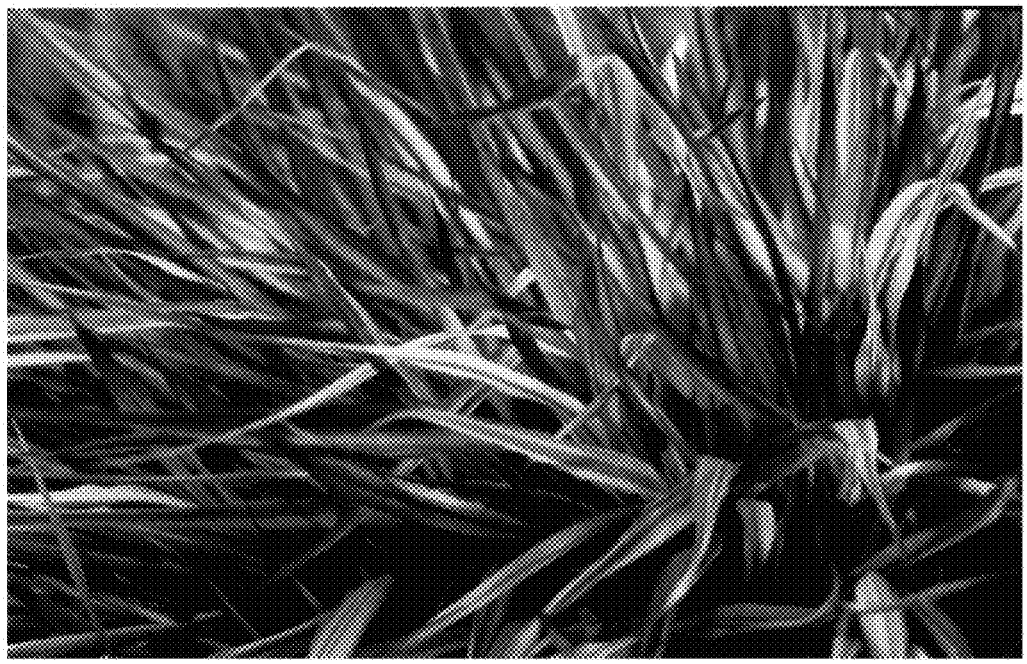

The photograph in FIG. 2 provides a close-up view of the fall foliage of 'LUCMULL'.

Figure 3:
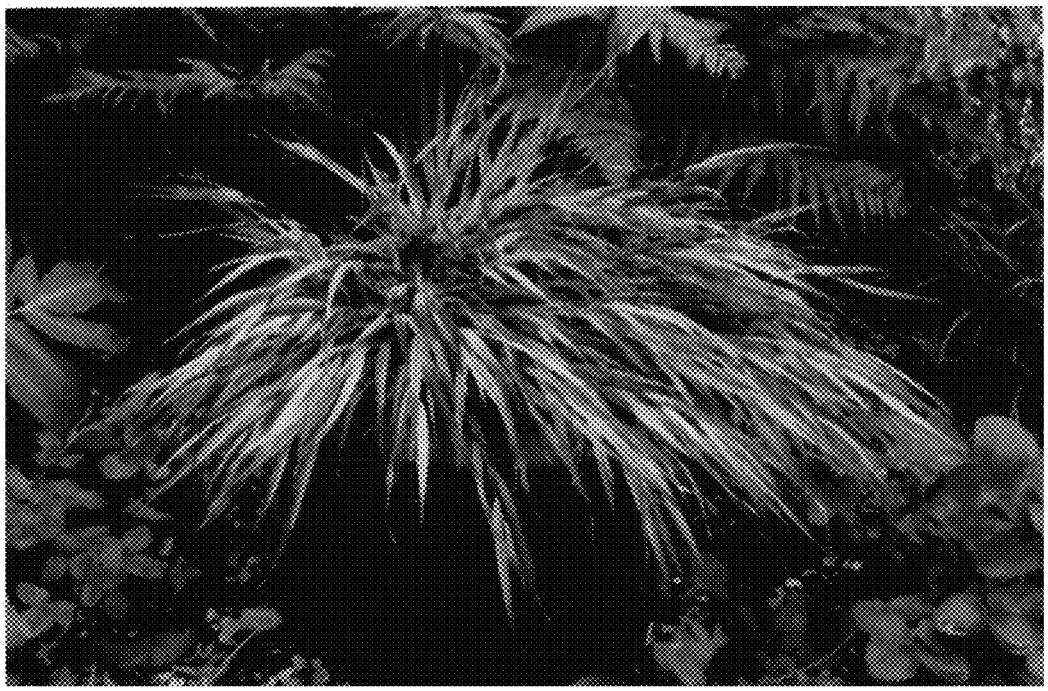

The photograph in FIG. 3 provides a view of the foliage of 'LUCMULL' in late summer in bloom.

The colors in the photographs may differ slightly from the color values cited in the detailed botanical description, which accurately describe the colors of the new *Hakonechloa.*

BOTANICAL DESCRIPTION OF THE PLANT

The following is a detailed description of 3-year-old plants of 'LUCMULL' as grown outdoors in 30-cm containers in Wimborne, Dorset, United Kingdom The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming habit.*—Insignificant flowers produced mid to late summer in the United Kingdom, grown as foliage plant.

*Plant type.*—Herbaceous ornamental grass.

*Plant habit.*—Compact plant habit forming a low growing rounded mound with a slightly upright spikeness to the blades.

*Height and spread.*—An average of 30 cm in height and 40 cm in spread as a 3-year-old plant in a container.

*Cold hardiness.*—At least to U.S.D.A. Zone 5.

*Diseases and pests.*—No susceptibility or resistance to diseases or pests has been observed.

*Root description.*—Fibrous.

*Propagation.*—Tissue culture and stem division.

*Growth rate.*—Slow.

*Root development.*—A finished young plant is produced from a division in about 12 weeks.

Culm (stem) description:

*General.*—Round, sheathed.

*Culm color.*—Young; 145A, mature; 151C, base 152D, internodes; 151A to 151B.

*Culm size.*—Average of 12.1 cm in length and 1.5 mm in width.

*Stem surface.*—Slightly glossy, glabrous.

*Stem strength.*—Strong.

*Stem number.*—Average of 40.

*Internode length.*—Average of 1.5 cm.

*Branch aspect.*—Average of 47.5°.

*Branching.*—Basal branches only, no lateral branches.

Foliage description:

*Leaf shape.*—Lanceolate.

*Leaf division.*—Simple.

*Leaf base.*—Leaf sheathing, lamina attenuate.

*Leaf apex.*—Narrowly acuminate.

*Leaf aspect.*—Held upward ata bout a 20° angle to vertical.

*Leaf venation.*—Parallel, upper surface color a blend of 155B and 160D, irregularly axially striped 143A, 144B, 144C and 147D, lower surface a blend of 155B and 160D, irregularly axially striped 143A, 144B, 144C and 147D.

*Leaf margins.*—Entire, slightly sharp to the touch when rubbed downward due to very small non-visible teeth, non-undulate.

*Leaf attachment.*—Sheathed.

*Leaf size.*—Average of 12.2 cm in length, 9 mm in width.

*Leaf number.*—Average of 8 per branch.

*Leaf arrangement.*—Alternate.

*Ligule.*—156D in color, moderately pubescent with very short hairs an average of 0.5 mm in length and 156D in color.

*Leaf surface.*—Both surfaces smooth, non-rugose and glabrous, upper surface very slightly glossy, lower surface matte.

*Leaf color.*—Young upper surface; 154B and 154C, irregularly axially striped N144C and N144D, young lower surface; 154C and 154D, irregularly axially striped 144B and 144C, mature upper surface; a blend of 155B and 160D, irregularly axially striped 144A, fall color; 183C and 183D, irregularly axially striped 151D, mature lower surface; a blend of 155B and 160D, irregularly axially striped 143A, 144B, 144C and 147D, fall color; 199D, slightly tinged 183D, irregularly axially striped 144A and 144B.

Inflorescence description:

*General description.*—Terminal airy panicle of single spikelets.

*Lastingness of inflorescence.*—Each panicle blooms for about 3 weeks, persistent.

*Fragrance.*—None.

*Panicle size.*—Average of 15 cm in length and up to 5 cm in width.

*Panicle number.*—One per culm.

*Rachis.*—An average of 5 cm in length, 0.7 mm in diameter, color; a blend of 155B and 160D, slightly tinged 183D, rachilla emerging to about a 60° angle to culm.

*Spikelet bud.*—About 1 cm in length and 2 mm in width, narrow lanceolate to ovate in shape, color; a blend of 155B and 160D, tinged 183C and 183D.

*Spikelet description.*—Single floret enclosed by one glume and one lemma, glume; lanceolate in shape with a glabrous surface, entire margin, acute apex, 8 mm in length, 1 mm in width, color; a blend of 155B and 160D, tinged 183D, lemma; lanceolate in shape with a glabrous surface, entire margin, acute apex, 6 mm in length, 1 mm in width and color; a blend of 155B and 160D, tinged 183D.

*Spikelet number.*—Average of 20 per panicle.

*Spikelet size.*—About 7 cm in length and 1 cm in width.

Reproductive organs:

*Stamens.*—2, anthers are dorsifixed, x-shaped, about 1.5 mm in length and 160D in color, pollen was not observed.

*Pistils.*—2, about 1 mm in length, stigma; fimbriate in shape, about 0.7 mm in length, and 155B in color, style; transparent in color, about 0.5 mm in length, ovary; 155B in color.

*Seed.*—Seed development has not been observed.

It is claimed:

1. A new and distinct cultivar of *Hakonechloa* plant named 'LUCMULL' as herein illustrated and described.

* * * * *